United States Patent
Govari et al.

(10) Patent No.: US 11,135,008 B2
(45) Date of Patent: Oct. 5, 2021

(54) GRAPHICAL USER INTERFACE (GUI) FOR DISPLAYING ESTIMATED CARDIAC CATHETER PROXIMITY TO THE ESOPHAGUS

(71) Applicant: Biosense Webster (Israel) Ltd., Yokneam (IL)

(72) Inventors: Assaf Govari, Haifa (IL); Ella Ozeri, Binyamina (IL); Andres Claudio Altmann, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 15/841,009

(22) Filed: Dec. 13, 2017

(65) Prior Publication Data
US 2019/0175265 A1    Jun. 13, 2019

(51) Int. Cl.
*G06T 11/20* (2006.01)
*A61B 18/14* (2006.01)
(Continued)

(52) U.S. Cl.
CPC ............ *A61B 18/1492* (2013.01); *A61B 5/06* (2013.01); *A61B 5/066* (2013.01); *A61B 34/10* (2016.02);
(Continued)

(58) Field of Classification Search
CPC ..... A61B 18/1492; A61B 90/37; A61B 34/25; A61B 2018/0022; A61B 2034/2065;
(Continued)

(56) References Cited

U.S. PATENT DOCUMENTS 5,391,199 A    2/1995    Ben-Haim
5,687,737 A    11/1997   Branham et al.
(Continued)

FOREIGN PATENT DOCUMENTS

WO    WO 96/05768 A1    2/1996
WO    15/063246          5/2015
WO    17/151576          9/2017

OTHER PUBLICATIONS

Pending U.S. Appl. No. 15/840,980, filed Dec. 13, 2017.
(Continued)

*Primary Examiner* — Saptarshi Mazumder
(74) *Attorney, Agent, or Firm* — Todd A. Noah; Dergosits & Noah LLP (57) ABSTRACT

An apparatus includes a processor and an output device. The processor is configured to receive positions, within a heart of a patient, of one or more electrodes that apply Radio Frequency (RF) energy to ablate tissue in the heart, in a coordinate system having a vertical axis. The processor is further configured to receive positions, within a heart of a patient, of one or more electrodes that apply Radio Frequency (RF) energy to ablate tissue in the heart, in a coordinate system having a vertical axis, and to calculate, based on the received positions, a subset of one or more smallest heights among respective heights of the electrodes above an esophagus of the patient along the vertical axis, and to generate a graphical user interface that visualizes the electrodes and the respective heights above the esophagus. The output device is configured to present the graphical user interface to a user.

10 Claims, 5 Drawing Sheets

(51) Int. Cl.

| | | |
|---|---|---|
| *A61B 34/00* | (2016.01) | |
| *A61B 5/06* | (2006.01) | |
| *A61B 34/20* | (2016.01) | |
| *A61B 34/10* | (2016.01) | |
| *A61B 90/00* | (2016.01) | |
| A61B 18/00 | (2006.01) | |
| A61B 6/12 | (2006.01) | |
| A61B 17/00 | (2006.01) | |

(52) U.S. Cl.
CPC ............ *A61B 34/20* (2016.02); *A61B 34/25* (2016.02); *A61B 90/37* (2016.02); *G06T 11/206* (2013.01); *A61B 6/12* (2013.01); *A61B 2017/00199* (2013.01); *A61B 2017/00243* (2013.01); *A61B 2018/0016* (2013.01); *A61B 2018/0022* (2013.01); *A61B 2018/00357* (2013.01); *A61B 2018/00375* (2013.01); *A61B 2018/00488* (2013.01); *A61B 2018/00577* (2013.01); *A61B 2018/00642* (2013.01); *A61B 2018/1467* (2013.01); *A61B 2034/2051* (2016.02); *A61B 2034/2053* (2016.02); *A61B 2034/2065* (2016.02); *A61B 2034/2072* (2016.02); *A61B 2090/061* (2016.02); *G06T 2200/24* (2013.01)

(58) Field of Classification Search
CPC .......... A61B 2017/00199; A61B 2018/00642; A61B 2018/00577; A61B 2018/00488; A61B 2018/00357; G06T 11/206; G06T 2200/24
See application file for complete search history.

(56) References Cited

U.S. PATENT DOCUMENTS

| | | | |
|---|---|---|---|
| 6,239,724 B1 | 5/2001 | Doron et al. | |
| 6,332,089 B1 | 12/2001 | Acker et al. | |
| 6,484,118 B1 | 11/2002 | Govari | |
| 6,618,612 B1 | 9/2003 | Acker et al. | |
| 6,690,963 B2 | 2/2004 | Ben-Haim et al. | |
| 7,756,576 B2 | 7/2010 | Levin | |
| 7,848,787 B2 | 12/2010 | Osadchy | |
| 7,848,789 B2 | 12/2010 | Govari et al. | |
| 7,869,865 B2 | 1/2011 | Govari et al. | |
| 8,456,182 B2 | 6/2013 | Bar-Tal et al. | |
| 8,863,742 B2* | 10/2014 | Blomquist | A61B 5/04884 128/204.23 |
| 2002/0065455 A1 | 5/2002 | Ben-Haim et al. | |
| 2003/0120150 A1 | 6/2003 | Govari | |
| 2004/0068178 A1 | 4/2004 | Govari | |
| 2006/0106375 A1 | 5/2006 | Werneth | |
| 2006/0116576 A1 | 6/2006 | McGee et al. | |
| 2006/0122514 A1 | 6/2006 | Byrd et al. | |
| 2006/0247721 A1* | 11/2006 | Maschino | A61F 5/0026 607/40 |
| 2007/0049817 A1 | 3/2007 | Preiss et al. | |
| 2007/0106289 A1 | 5/2007 | O'Sullivan | |
| 2007/0225593 A1* | 9/2007 | Porath | A61B 5/06 600/423 |
| 2008/0085042 A1 | 4/2008 | Trofimov et al. | |
| 2010/0168735 A1 | 7/2010 | Deno et al. | |
| 2010/0202678 A1 | 8/2010 | Kobayashi | |
| 2010/0217116 A1 | 8/2010 | Eck | |
| 2010/0249771 A1* | 9/2010 | Pearson | A61B 18/1206 606/34 |
| 2011/0144521 A1 | 6/2011 | Molnar et al. | |
| 2011/0264165 A1 | 10/2011 | Molnar et al. | |
| 2016/0051321 A1* | 2/2016 | Salahieh | A61B 1/00082 600/439 |

OTHER PUBLICATIONS

European Search Report and Written Opinion for European Application No. 182110843.0; dated May 14, 2019.
European Search Report for corresponding EPA No. 18211843.0 dated Jul. 14, 2020.

* cited by examiner

GRAPHICAL USER INTERFACE (GUI) FOR DISPLAYING ESTIMATED CARDIAC CATHETER PROXIMITY TO THE ESOPHAGUS

CROSS-REFERENCE TO RELATED APPLICATIONS

This application is related to a U.S. patent application Ser. No. 15/840,980,entitled "Estimating Cardiac Catheter Proximity to the Esophagus," filed Dec. 13, 2018, whose disclosure is incorporated herein by reference.

FIELD OF THE INVENTION

The present invention relates generally to invasive medical devices and methods of treatment, and specifically to monitoring the position of an ablation probe within a living body.

BACKGROUND OF THE INVENTION

Systems for obtaining real-time spatial information on objects placed within a living body are often utilized for the monitoring of invasive treatments. The monitoring sometimes involves registration of the spatial information with medical images taken by another imaging modality. For example, U.S. Patent Application Publication 2008/0085042 describes a method for imaging that includes receiving a first three-dimensional (3D) image of a vicinity of an organ within a body of a subject and creating a geometrical model of a tubular structure in the first 3D image in the vicinity of the organ. An invasive probe is inserted into the organ, and a second 3D image containing the organ is captured using the invasive probe. One or more points are located on a surface of the tubular structure using the invasive probe, and the second 3D image is registered with the first 3D image by matching the one or more points to the geometrical model.

As another example, U.S. Patent Application Publication 2007/0225593 describes a device for enhancing visualization of an esophagus when imaged by a visualization system. The device comprises a structure including material that is clearly visible when imaged by the visualization system. The structure is arranged, when inserted into the esophagus, to expand so as to conform to an inner surface of the esophagus in order to enhance a visualization quality of the surface when imaged by the visualization system. A cord attached to the structure is arranged to extend out of the esophagus so as to assist a removal of the device from the esophagus.

U.S. Pat. No. 8,456,182 describes a method that includes positioning body-electrodes in galvanic contact with a body of a patient and positioning a mapping-tool, having a mapping-electrode, in a plurality of regions in the body. The method further includes tracking the mapping-tool at different positions in each of the regions using a location-measuring system, and for each region, generating a respective set of calibration-currents between the body-electrodes and the mapping-electrode at the different positions in the region. A respective relation is derived for each region between the respective set of the calibration-currents and the different positions, and is used in determining the location of an investigation-tool in response to the different respective relations and investigation-tool-currents.

U.S. Patent Application Publication 2006/0116576 describes systems and method for navigating a medical probe relative to the heart. A mark (such as a point or a line), representing an anatomical region of interest (such as tissue targeted for treatment or tissue not targeted for treatment) is displayed on a representation of the anatomical body. The positions of the medical probe and the mark are determined within a three-dimensional coordinate system, and the proximity between the medical probe and the mark determined based on these positions. This proximity can then be indicated to a user, e.g., using graphics, text, or audible sounds.

U.S. Patent Application Publication 2007/0049817 describes systems and methods for registering maps with images, involving segmentation of three-dimensional images and registration of images with an electro-anatomical map using physiological or functional information in the maps and the images, rather than using only location information. A typical application of the invention involves registration of an electro-anatomical map of the heart with a pre-acquired or real-time three-dimensional image. Features such as scar tissue in the heart, which typically exhibits lower voltage than healthy tissue in the electro-anatomical map, can be localized and accurately delineated on the three-dimensional image and map.

SUMMARY OF THE INVENTION

An embodiment of the present invention provides an apparatus including a processor and an output device. The processor is configured to receive positions, within a heart of a patient, of one or more electrodes that apply Radio Frequency (RF) energy to ablate tissue in the heart, in a coordinate system having a vertical axis. The processor is further configured to calculate, based on the received positions, a subset of one or more smallest heights among respective heights of the electrodes above an esophagus of the patient along the vertical axis. The output device is configured to present to a user an indication of the smallest heights.

In some embodiments, the subset of smallest heights consists of a single smallest height.

In some embodiments, the processor is configured to adjust RF ablation parameters of the one or more electrodes responsively to the subset of smallest heights.

In an embodiment, the processor and the output device are configured to calculate the one or more smallest heights and present to a user an indication of the smallest heights, respectively, at a given rate or by request.

In another embodiment, the processor is configured to receive one or more medical images that image at least part of the esophagus and at least part of the heart, and to calculate the subset of smallest heights based on the positions and on the medical images.

In some embodiments, the output device is configured to present to a user a value of each of the smallest heights.

In some embodiments, the processor is configured to calculate the positions of the one or more electrodes based on estimated position and orientation of a position sensor coupled to the one or more electrodes.

There is additionally provided, in accordance with an embodiment of the present invention, a method including, in a processor, receiving positions, within a heart of a patient, of one or more electrodes that apply Radio Frequency (RF) energy to ablate tissue in the heart, in a coordinate system having a vertical axis. Based on the received positions, a subset of one or more smallest heights among respective heights of the electrodes above an esophagus of the patient along the vertical axis is calculated. An indication of the smallest heights is presented to a user.

Another embodiment of the present invention provides an apparatus including a processor and an output device. The processor is configured to receive positions, within a heart of a patient, of one or more electrodes that apply Radio Frequency (RF) energy to ablate tissue in the heart, in a coordinate system having a vertical axis. The processor is further configured to receive positions, within a heart of a patient, of one or more electrodes that apply Radio Frequency (RF) energy to ablate tissue in the heart, in a coordinate system having a vertical axis, and to calculate, based on the received positions, a subset of one or more smallest heights among respective heights of the electrodes above an esophagus of the patient along the vertical axis, and to generate a graphical user interface that visualizes the electrodes and the respective heights above the esophagus. The output device is configured to present the graphical user interface to a user.

In some embodiments, the graphical user interface includes a diagram that displays a geometrical arrangement of the one or more electrodes.

In some embodiments, the geometrical arrangement of the one or more electrodes visualizes an actual physical arrangement of the electrodes relative to the esophagus.

In an embodiment, the graphical user interface displays, for each electrode, a respective identifier.

In another embodiment the processor is configured to update the graphical user interface at a given rate or by request.

In some embodiments, the processor is configured to receive one or more medical images that image at least part of the esophagus and at least part of the heart, and to calculate the subset of smallest heights based on the positions and on the medical images. The processor is further configured to estimate a value for each of the heights among the subset of smallest heights, and to generate the graphical user interface, wherein the graphical user interface displays the value estimated for each of the calculated heights.

There is additionally provided, in accordance with an embodiment of the present invention, a method including, in a processor, receiving positions within a heart of a patient, in a coordinate system having a vertical axis, of one or more electrodes that apply Radio Frequency (RF) energy to ablate tissue in the heart. Based on the received positions, a subset of one or more smallest heights among respective heights of the electrodes above an esophagus of the patient along the vertical axis is calculated. A graphical user interface is generated, which visualizes the electrodes and the respective heights above the esophagus. The graphical user interface is displayed to a user.

The present invention will be more fully understood from the following detailed description of the embodiments thereof, taken together with the drawings in which:

DETAILED DESCRIPTION OF EMBODIMENTS

Overview

The proximity of the esophagus to the left atrium of the heart can cause problems in catheter ablation of target tissue in the left atrium, such as pulmonary vein isolation procedures that are used in treating atrial fibrillation. The esophagus lies posterior to the left atrium and traverses a variable course relative to the left atrium, adjacent to the right or left pulmonary vein or the posterior wall of the heart. Hence, there is a risk of esophageal damage due to the high temperatures occurring when ablation is performed in the posterior left atrium.

One possible way to prevent this sort of damage is to use an esophageal probe fitted with temperature sensors to give an indication of heating of the esophagus. In some cases, however, the indication may take time, and may be too late to prevent damage. Moreover, esophageal probes cause patient discomfort and may themselves cause damage and generally complicate the procedure.

Embodiments of the present invention that are described herein provide systems and methods that protect the esophagus from thermal damage during the cardiac ablation without having to insert any object into the esophagus. In the disclosed embodiments, a medical instrument such as a catheter, comprising one or more Radio-Frequency (RF) ablation electrodes at its distal end, is inserted into the left atrium. Since the patient is known to lie on his back, the vertical (z-axis) positions of the ablation electrodes are necessarily above the esophageal tissue.

In some embodiments, a processor sorts the ablation electrodes based on their relative heights. Based on these derived relative heights above the esophagus, the processor can automatically (and/or the physician can manually), adjust the ablation procedure so as to prevent thermal damage from lower ablation electrodes. In an embodiment, the processor is further configured to adjust the specific RF ablation parameters of individual electrodes responsively to the sorted list of relative heights of the electrodes.

In some embodiments, the processor estimates the minimal vertical distance between the ablation electrodes and the esophagus. This distance is used as a simple but effective metric for assessing the risk of damage to the esophagus. The processor typically indicates the minimal vertical distance to the physician, who may in turn adjust the ablation procedure so as to prevent such damage.

In the description hereinafter, for simplicity, the term 'height' is mostly used instead of the terms 'vertical distance' or 'z-axis distance.' All three terms are used interchangeably.

In some embodiments, the procedure of estimating the minimal height begins with a processor receiving medical images that capture a patient's esophagus anatomy. A location of an esophageal tissue considered at risk of collateral thermal damage is then marked on the received medical images.

The minimal height estimation procedure continues with the processor receiving the ablation electrodes positions in the left atrium. In some embodiments, obtaining the electrode positions is assisted by a position-tracking and ablation system.

The processor then registers the positions of the electrodes with the received medical images. Image registration is defined herein as the process of transforming different sets of data into one coordinate system.

The processor then calculates the heights of one or more of the registered electrodes positions above the marked esophageal tissue at risk. The minimal height (i.e., the vertical distance between the esophagus and the nearest ablation electrode) is indicated to the physician.

As said above, the physician may consider to use the height information in the course of planning the ablation treatment. The physician may, for example, limit the level of electrical power and/or the duration of the application of the electrical energy of the electrodes possessing the minimal height above the esophagus.

In some embodiments, a minimal height threshold is set. Ablation electrodes having heights below threshold are considered, in the course of planning the ablation treatment, for example, for limiting the level of electrical power and/or the duration of the application of the electrical energy.

In some embodiments, the processor displays to the physician a Graphical User Interface (GUI) comprising a diagram that presents the arrangement of the ablation electrodes on a display. The diagram typically shows the electrode locations relative to the esophagus and, in some embodiments, provides their respective heights above the esophagus tissue at risk. The GUI further highlights the one or more electrodes closest to the esophagus and/or updates the electrodes arrangement on the display according to their heights. The physician may utilize the diagram to make further decisions, such as to deactivate one or more of the electrodes. Alternatively or additionally, the processor may use the information presented by the diagram to automatically adjust (or propose adjusting) one or more ablation parameters. In an embodiment, the processor issues a warning and/or a value limit regarding the allowed RF power to the physician.

The validity of the disclosed technique stems from the similar patient postures during the acquisition of the medical images and during the ablation procedure. In both cases the patient lays still on his back, wherein the esophagus is consistently positioned below the heart, making image registration a viable approach for distance estimation. Moreover, catheterization rooms are regularly equipped with fluoroscopes or other imaging equipment, opening the possibility to acquire the required medical images in situ.

The disclosed technique has distinct advantages over other possible solutions in that it eliminates the need to insert any kind of object into the esophagus. Thus, for example, the disclosed technique reduces the number of invasive activities taken during the cardiac ablation procedure. The disclosed technique also avoids discomfort and potential injury to the patient that esophagus probes may cause.

System Description

Figure 1A:
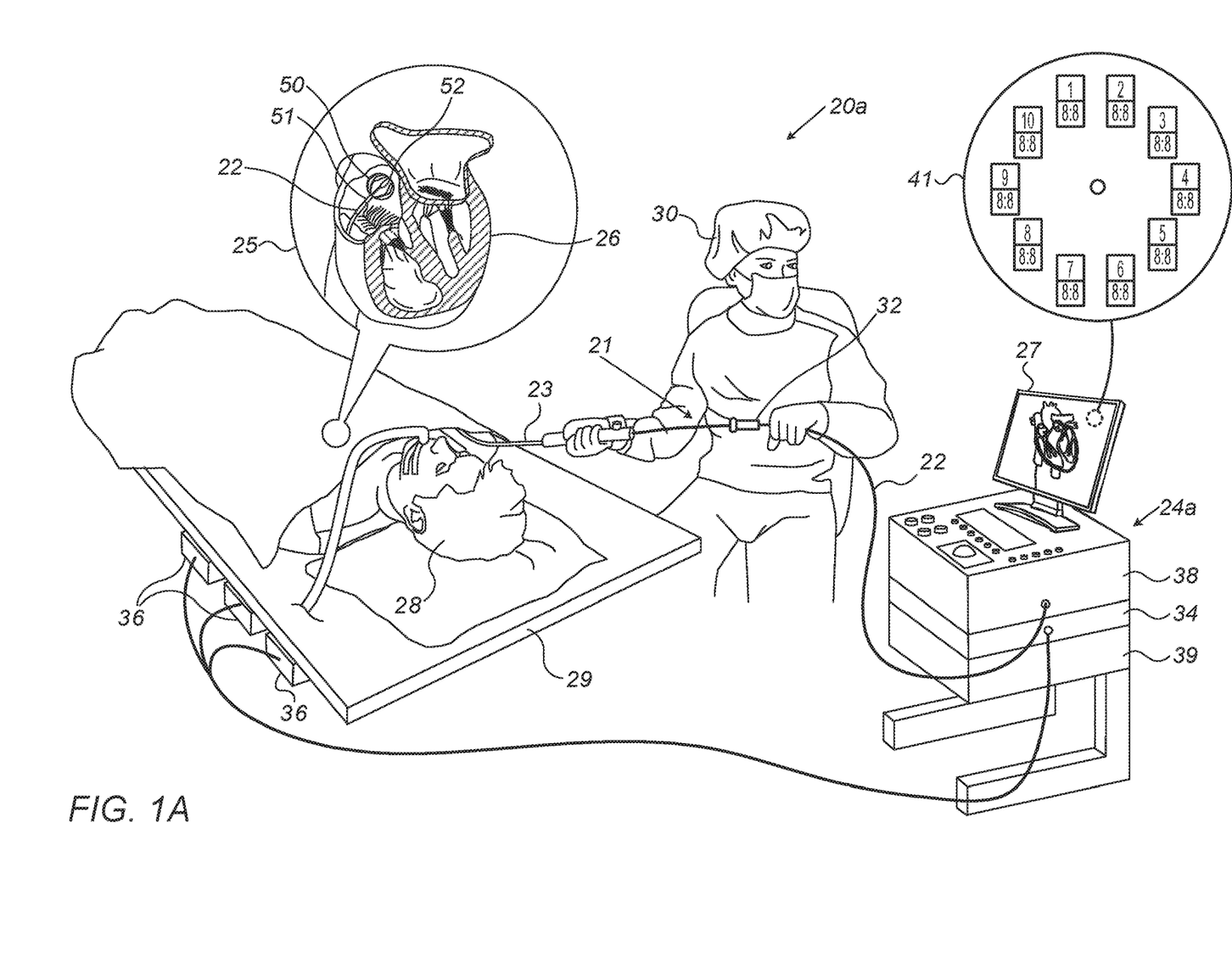
FIGS. 1A and 1B are schematic, pictorial illustrations of two catheter-based position-tracking and ablation systems, in accordance with some embodiments of the present invention.
Figure 1B:
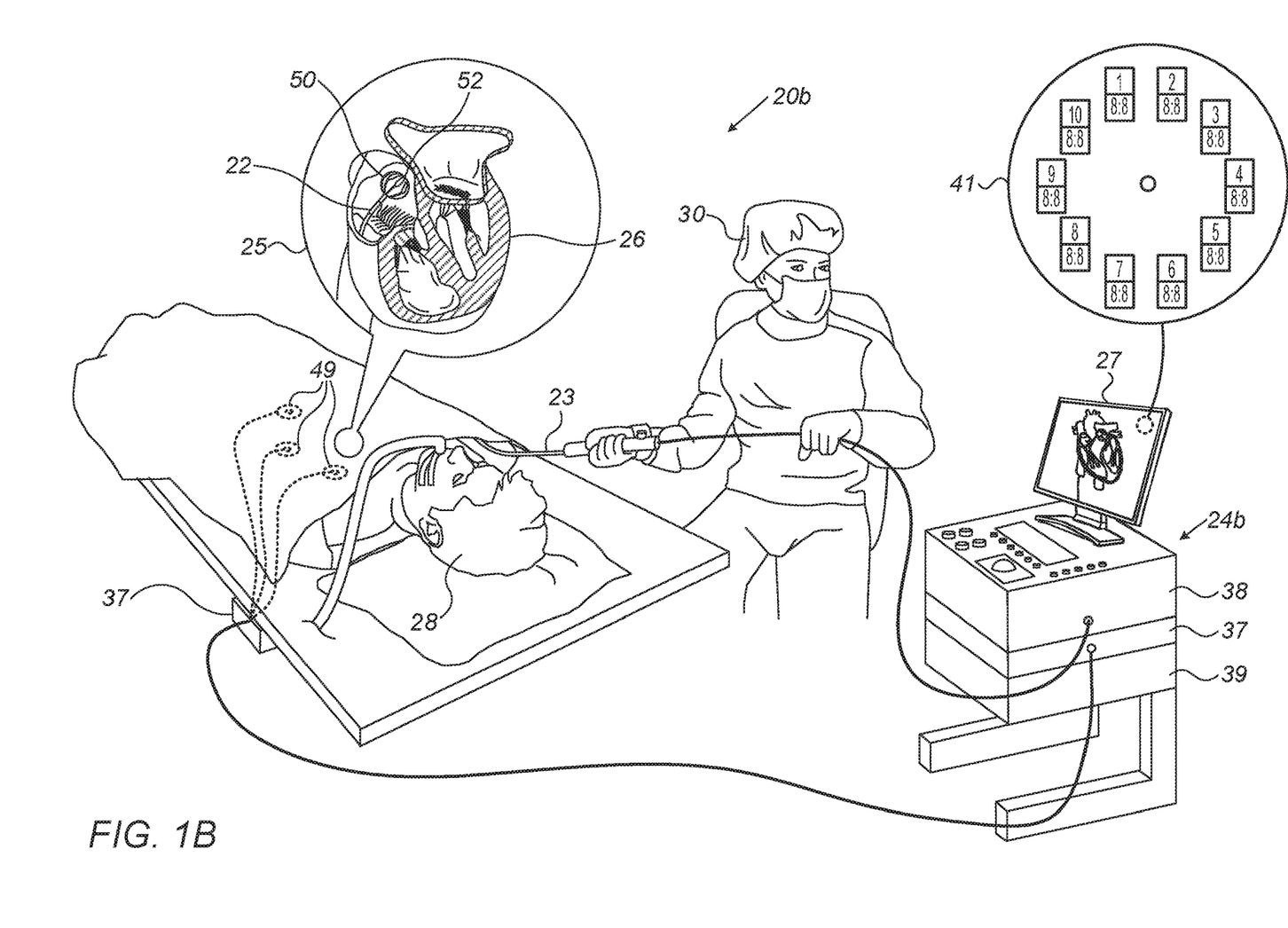

FIGS. 1A and 1B are schematic, pictorial illustrations of two catheter-based position-tracking and ablation systems, in accordance with some embodiments of the present invention.

FIG. 1A illustrates a magnetic sensing catheter-based position-tracking and ablation system 20a. System 20a comprises a catheter 21, having a shaft distal end 22 that is navigated by a physician 30 into a heart 26 of a patient 28 via the vascular system. In the pictured example, physician 30 inserts shaft distal end 22 through a sheath 23, while manipulating the distal end of shaft distal end 22 using a manipulator 32 near the proximal end of the catheter. As shown in an inset 25, shaft distal end 22 comprises a magnetic sensor 51 contained within the shaft distal end 22 and a balloon 50. (The balloon is inserted through sheath 23 in a deflated state and is then inflated within heart 26).

In the embodiments described herein, catheter 21 is used for ablation of tissue in heart 26. Although the pictured embodiment relates specifically to the use of a balloon catheter for ablation of heart tissue, the elements of system 20a and the methods described herein may alternatively be applied in controlling ablation using other sorts of multi-electrode catheters, such as lasso, basket, and multi-arm catheters.

The proximal end of catheter 21 is connected to a control console 24a. Console 24a comprises a processor 39, typically a general-purpose computer, with suitable front end and interface circuits 38 for receiving signals from catheter 21, as well as for applying energy via catheter 21 to ablate tissue in heart 26 and for controlling the other components of system 20a. Console 24a also comprises a driver circuit 34, configured to drive magnetic field generators 36.

During the insertion of shaft distal end 22, balloon 50 is maintained in a collapsed configuration. Once shaft distal end 22 has reached the target location within heart 26, physician 30 inflates balloon 50. Console 24a receives signals from magnetic sensor 51 in response to magnetic fields from external field generators 36, for example, for the purpose of measuring the position of balloon 50 in the heart. Magnetic field generators 36 are placed at known positions external to patient 28, e.g., below a table 29 on which the patient is lying. These position signals are indicative of the position of inflated balloon 50 in the coordinate system of the position tracking system.

This method of position sensing using external magnetic fields is implemented in various medical applications, for example, in the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

In some embodiments, processor 39 is configured to receive medical images that captured at least part of the patient's esophagus anatomy and at least part of the heart anatomy. Processor 39 may be further configured to apply segmentation algorithm on the received images to delineate the esophagus as to assist physician 30 to identify the esophagus tissue at risk. In an alternative embodiment, the heart anatomy may be delineated as well. Processor 39 may be configured to receive position signals from magnetic sensor 51, derive the positions of electrodes 52, and register the positions of electrodes 52 with the received medical images. Processor 39 can then calculate the estimated heights above the esophagus tissue at risk, of the one or more of the closest electrodes to the esophagus. Furthermore, processor 39 may be configured to present the distance information on a suitable output device, e.g., a monitor 27, using a GUI.

In an optional embodiment, processor 39 is further configured to estimate the orientation of shaft distal end 22, based on the signals from magnetic sensor 51, and further estimates the location of the ablation electrodes relative to the esophagus responsively to the estimated orientation and display the arrangement of electrodes 52 on monitor 27 in the form of diagram 41 using the GUI.

Processor 39 typically comprises a general-purpose computer, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

In some embodiments, additionally or alternatively, a position-tracking and ablation system may comprise and use an Active Current Location (ACL) sub-system 37 to identify electrodes 52 and to estimate electrodes 52 heights above the esophagus.

FIG. 1B is a schematic, pictorial illustration of ACL sub-system 37 included in catheter-based position-tracking and ablation system 20b, in accordance with an embodiment of the present invention. As illustrated in FIG. 1B, ACL sub-system 37 comprises external sensing electrodes 49, which are attached to the patient's skin at the chest area. Sensing electrodes 49 generate position signals in response to current-signals injected by ablation electrodes 52. Based on the signals it receives from sensing electrodes 49, console 24b estimates the positions of ablation electrodes 52, for example using processor 39, and further estimates the distances between one or more of electrodes 52 and the esophagus tissue at risk. Thus, ACL sub-system 37 uses ablation electrodes 52 themselves for obtaining position signals related electrodes 52 locations.

The ACL method usually requires a calibration step, wherein a different, sensing calibration catheter is inserted to the left atrium, acquires a data set required for the calibration and then retracted. The method of electrodes position sensing using ACL is implemented in various medical applications, for example, in the CARTO™ system, produced by Biosense Webster Inc. (Diamond Bar, Calif.) and is described in detail in U.S. Pat. Nos. 8,456,182, 7,756,576, 7,869,865, 7,848,787, and 7,848,789, whose disclosures are all incorporated herein by reference. Other than the position-tracking feature, systems 20a and 20b share the same components required for planning and performing the ablation. Alternatively, the principles of the present invention may be implemented, once the necessary changes have been made, using other position sensing technologies that are known in the art, such as ultrasonic or impedance-based position sensing.

In some embodiments, systems 20a and 20b are fully fitted with processors, such as processor 39, configured for obtaining the estimated electrode distances. In another embodiment, the hardware and software required for at least part of the processing steps, such image-registration, comprises commercially available workstation fitted with a commercially available image processing software. In some embodiments, consoles 24a and 24b are configured to graphically present a diagram 41 on monitor 27, showing electrodes 52 arrangement and heights above the esophagus.

The configured processors may be an integral part of the treatment room equipment, for example part of a C-arm imaging modality. Alternatively, the configured processors may be located elsewhere at the hospital and the results sent to the physician by the hospital's communication system such as, a picture archiving and communication system (PACS).

Figure 2A:
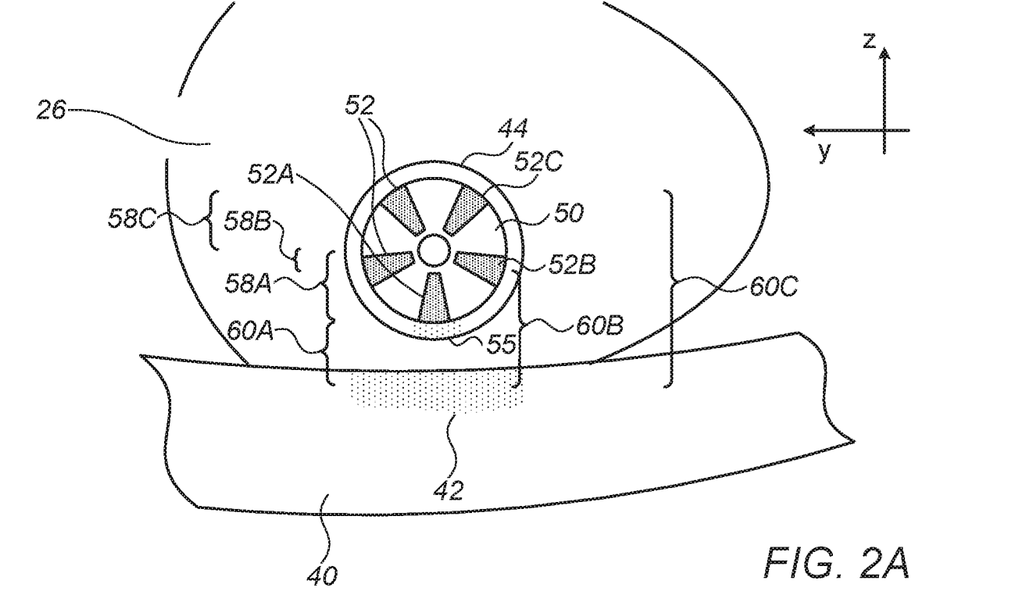
FIGS. 2A and 2B are schematic, cross-sectional illustrations showing details of an ablation catheter positioned at an ostium of a pulmonary vein and its relation to the esophagus, in accordance with an embodiment of the present invention.
Figure 2B:
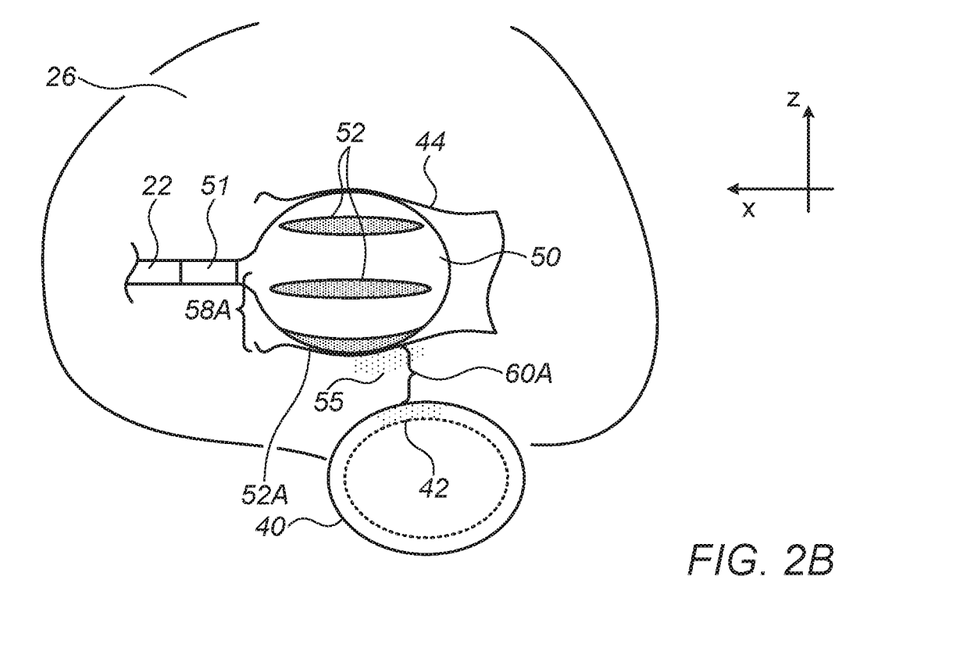

GUI for Displaying GUI for Displaying Estimated Cardiac Catheter Proximity to the Esophagus FIGS. 2A and 2B are schematic, cross-sectional illustrations showing details of an inflated balloon positioned at an ostium of a pulmonary vein and its relation to the esophagus, in accordance with an embodiment of the present invention.

FIG. 2A is a side view that illustrates the anatomical relationship between an ostium 44 and an esophagus 40 of a patient lying on his back. The vertical axis (z-axis) shown in the figure represents height above table 29. Physician 30 may inspect the patient's actual anatomy in the received medical images. As seen, ostium 44 lays above esophagus 40 (since the patient is lying on his back). An esophageal location considered at risk of collateral thermal damage is marked in the received medical images. The marking may be done automatically, for example by a segmentation algorithm, or performed manually by physician 30.

FIG. 2A also presents a front-view of balloon 50 positioned in physical contact with ostium 44 of a pulmonary vein within heart 26. Inflated balloon 50 comprises ablation electrodes 52 distributed around its outer surface for ablating ostium tissue 55.

A set of distances 60A, 60B, and 60C denotes the distances along the z-axis between electrodes 52A, 52B and 52C, and an esophagus tissue 42 at risk, respectively. In some embodiments, the positions of electrodes 52 are directly obtained and registered on the medical images. For example, when the ACL method described above is used, the approximate positions of electrodes 52 are found directly by the ACL sub-system itself. Processor 39 (used in some embodiments) registers electrodes 52 positions with the received medical images. Esophagus locations, such as the position of esophagus tissue 42 at risk, are marked on the received medical images, as described above. Processor 39 then calculates estimated distances 60, as the vertical length on received medical images between respective electrode positions and esophagus tissue 42. In the present example, distance 60A is the smallest, being between the closest electrode 52A and esophagus tissue 42 at risk.

In some cases, the positions of electrodes 52 may not be directly obtained, for example when ACL sub-system is unavailable. In some embodiments, as described above, ablation system 20a uses magnetic sensor 51 (seen in FIG. 1A and FIG. 2B) in order to identify the location and orientation of each and every one of electrodes 52 within the left atrium. System 20a may measure these locations and orientations based, for example, on the rotation angle of inflated balloon 50 relative to the z-axis, as indicated by the estimated orientation of shaft distal end 22. In the present example, electrode 52A is identified as the lowest, e.g., closest electrode to the esophagus, and the one most likely facing directly esophagus 40.

Thus, in some embodiments, in order to derive distances 60, the system will have first to calculate distances 58 per each electrode, which are related to the balloon geometry and to the orientation of electrodes 52 relative to esophagus tissue 42, as described below.

FIG. 2B illustrates schematically the anatomical relationship of ostium 44 and esophagus 40, from another perspective. As seen, magnetic sensor 51 is fitted at shaft distal end 22. The position signals that magnetic sensor generates enables measuring its position in the coordinate system of position tracking and ablation system 20a, as detailed in the system 20a description section above. Namely, to readily derive the height of magnetic sensor 51 above esophageal tissue 42.

Using the known balloon geometry, processor 39 (used in some embodiments) calculates distances 58 and relative orientations of each of electrodes 52 relative to magnetic sensor 51. As an example, FIG. 2A shows distances 58A, 58B and 58C between shaft distal end 22 (which includes magnetic sensor 51) and electrode 52A, 52B and 52C, respectively.

In the example horizontal positioning of shaft distal end 22 shown in FIGS. 2A and 2B, distances 58 denote the maximal heights of the electrodes above or below the center of balloon 50. As seen, electrode 52A is located a distance 58A below the balloon center (i.e. below magnetic sensor vertical position). As distance 58A is the maximal transverse radius of balloon 50, distance 60A between electrode 52A and esophagus tissue 42 is the smallest possible. On the other hand, electrode 52C is almost at the top of balloon 50, which contributes a distance 58C (approximately the balloon radius) to the total length 60C between electrode 52C and esophagus tissue 42.

At same time, electrode 52B is almost at the same level as shaft distal end 22, making 58B a small correction, making 52B height above tissue 42 to be very similar to the measured height of shaft distal end 22 (i.e. of magnetic sensor 51).

Processor 39 is now capable of providing the electrodes 52 positions in the coordinate system of system 20a and to register electrodes 52 with the received medical images. Finally, estimated distances 60 between electrodes 52 and the esophagus tissue 42 are calculated as explained above.

The example configurations shown in FIGS. 2A and 2B are chosen purely for the sake of conceptual clarity. Any other suitable configurations can be used in alternative embodiments. For example, numerous distances can be estimated, such as these between one or more electrodes 52 and one or more marked esophagus locations. In some balloon orientations, two or more of electrodes 52 might be the closest to the esophagus.

In some embodiments, a range of distances, below certain given threshold is considered, which may yield a partial subset of the ablation electrodes, which have heights below the given threshold. In the course of planning the ablation treatment, the group of electrodes are considered as having a height below certain minimum (threshold) height.

In some embodiments, only relative heights of the ablation electrodes are derived (i.e., the ablation electrodes are identified and sorted by their relative heights without resorting to quantitative estimations of the actual distances).

In FIGS. 2A and 2B shaft distal end 22 is illustrated as directed horizontally, for simplicity. Yet in general, shaft distal end 22 may have any direction in space. Thus, usually the calculation of distances 60 shall include calculating projections values that depend on the on the angle between shaft distal end 22 and the vertical axis.

System 20 may comprise other sorts of ablation devices, such as a circular multi-electrode catheter (e.g., the Lasso® catheter made by Biosense Webster Inc.) or a multi-branch multi-electrode catheter (e.g., PentaRay® made by Biosense Webster Inc.). The medical images can be acquired by various imaging modalities such as C-arm fluoroscopy, CT, or MRI.

Figure 3:
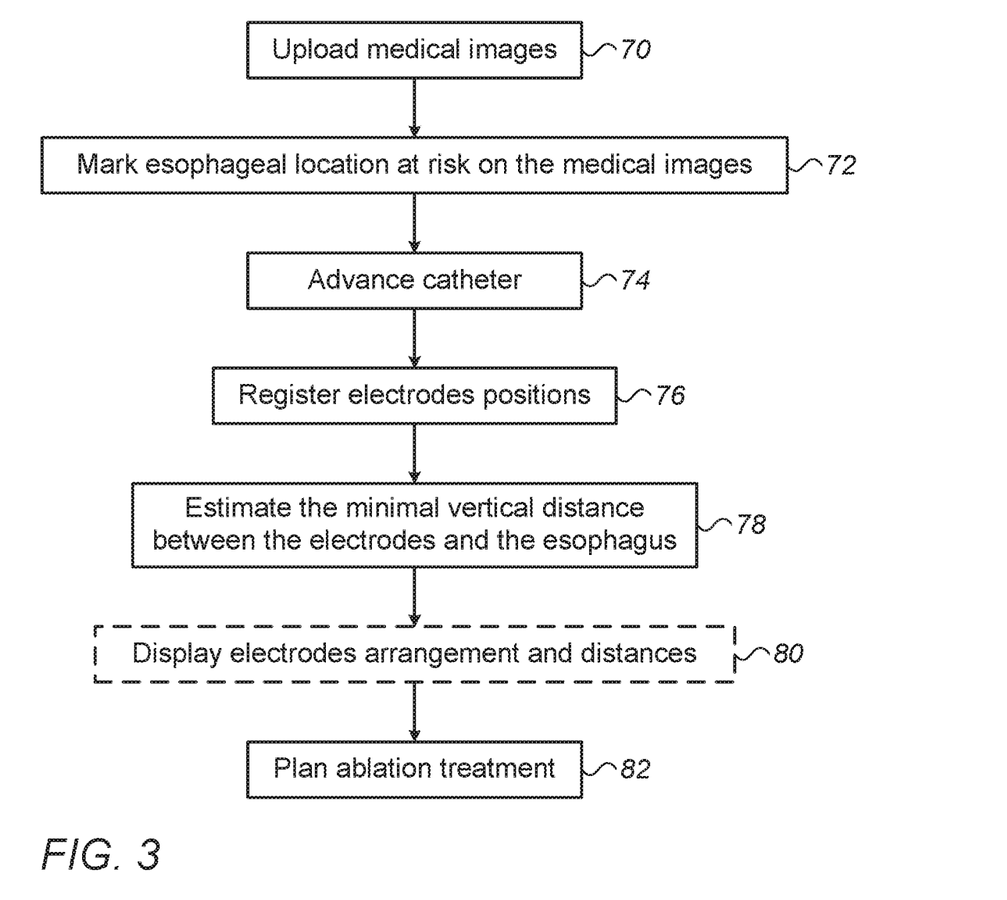
FIG. 3 is a flow chart that schematically illustrates a method for estimating heights of ablation electrodes above the esophagus, in accordance with an embodiment of the present invention.

FIG. 3 is a flow chart that schematically illustrates a method for estimating heights of RF ablation electrodes above the esophagus, in accordance with an embodiment of the present invention. The procedure begins with processor 39 receiving medical images comprising at least part of the esophagus and the heart anatomies of the patient, at an uploading step 70.

Physician 30 then marks the location of esophagus tissue 42 at risk on the received medical images, at a marking step 72. At an advancement step 74, physician 30 advances catheter's shaft distal end 22 into the patient's heart, and inflates and positions balloon 50 at the target tissue within the left atrium.

At a registration step 74, processor 39 calculates the positions of electrodes 52 and registers electrodes 52 positions with the received medical images. The marking may be done, for example, by a segmentation algorithm, or performed manually by physician 30.

At an Estimation step 78, processor 39 calculates the estimated height of each registered electrodes 52 above the marked location of esophagus tissue 42 at risk. Processor 39 selects the minimal height between electrodes 52 and esophagus tissue 42 at risk. Processor 39 indicates this minimal height to physician 30, e.g., on monitor 27.

In an optional embodiment, a GUI displays electrodes 52 arrangement on monitor 27, relative to the esophagus tissue 42, at a displaying step 80. The GUI shows an electrodes arrangement diagram 41, for example schematically arranged over a circle, and provides each of their respective distances to a marked esophagus location, such as the esophagus tissue 42 at risk.

In a planning step 82, physician 30 uses the electrodes identity and distance information to set ablation parameters, such as the maximal current and temperature of one or more of the electrodes. In some cases, physician 30 may disable RF power to one or more of the closest electrodes to the esophagus, such as for example electrode 52a in FIG. 2.

The example flow chart of FIG. 3 is shown purely for the sake of conceptual clarity. In alternative embodiments, the disclosed technique may use different and/or additional steps. For example, the physician may acquire new medical images from imaging equipment located within the catheterization room, such as a C-arm fluoroscope, then obtain updated electrode distances, and re-set one or more of the ablation parameters before applying the treatment.

In some embodiments, the disclosed technique uses Digital Imaging and Communications in Medicine (DICOM) format medical images. The DICOM format medical images may be acquired prior to the ablation procedure by a noninvasive imaging modality such as C-arm fluoroscopy, CT, or MRI.

Although some of the embodiments described herein mainly address processing of DICOM images, the methods and systems described herein can also be used in with other formats of medical images, such as Medical Imaging NetCDF (MINC).

Figure 4:
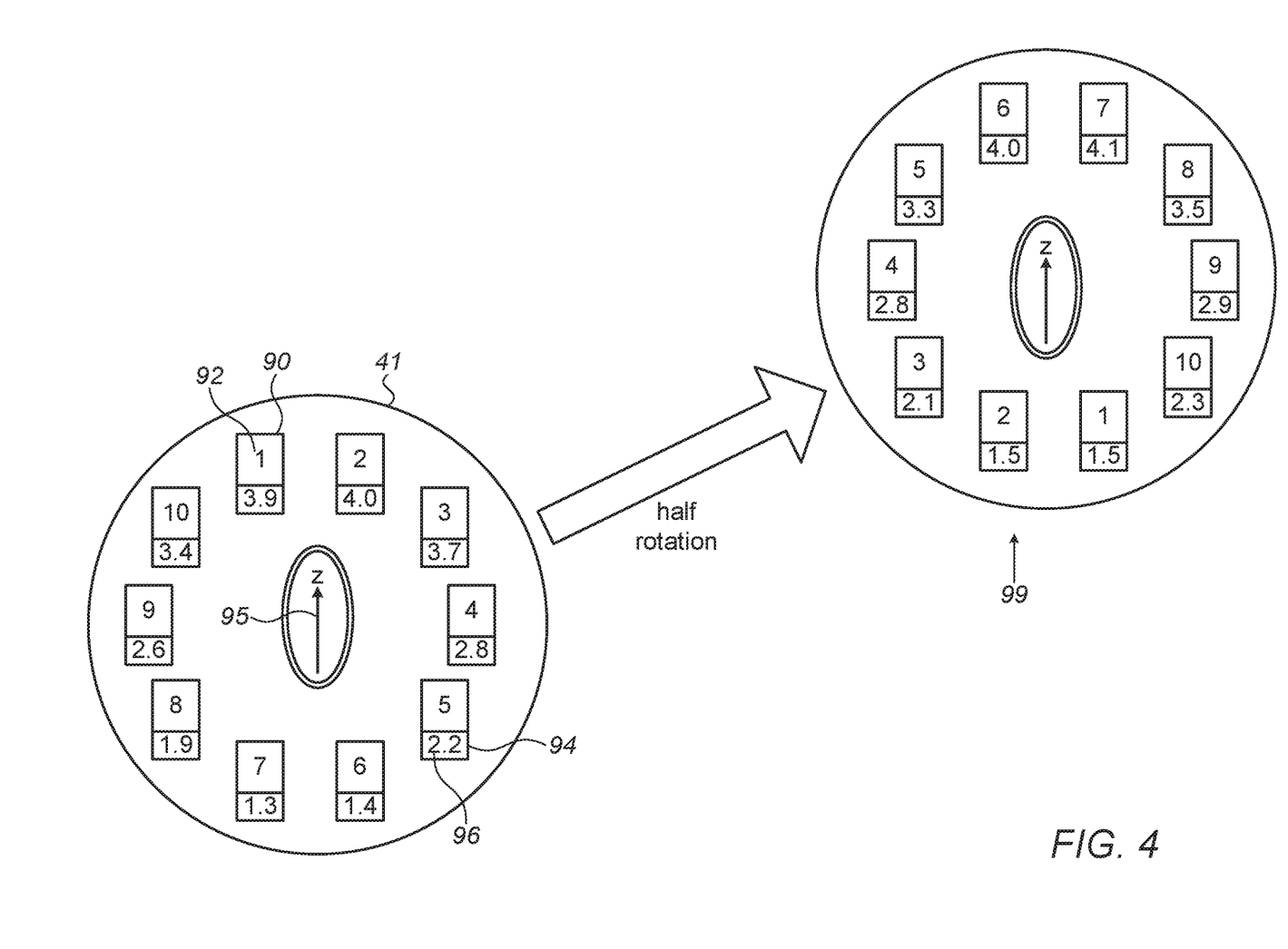
FIG. 4 is a schematic, pictorial illustration showing a graphical user interface, which presents estimated heights of ablation electrodes above the esophagus, in accordance with an embodiment of the present invention.

FIG. 4 is a schematic, pictorial illustration showing diagram 41, which presents the arrangement and estimated heights of ablation electrodes 52 above the esophagus, in accordance with an embodiment of the present invention. Diagram 41 is displayed by processor 39 on monitor 27.

In some embodiments, electrodes 52 are identified in diagram 41 with integer numbers 92 displayed in fields 90. Attached to fields 90 are fields 94 that display respective estimated heights 96 of electrodes 52 above the esophagus. Fields 94 may display heights 96 in centimeters and/or millimeters, for example. The vertical axis is marked in diagram 41 as a 'z' arrow 95, enabling the physician to recognize which of the electrodes are vertically lower, namely closer to the esophagus.

In an embodiment, processor 37 updates diagram 41 at a given rate and/or upon request by physician 30. The arrangement of electrode fields 90 and 94 within the diagram reflects the actual arrangement of the electrode relative to the esophagus. For example, in a case of a balloon catheter maneuver that involves half rotation of shaft distal end 22, electrodes 6 and 7 which are initially shown in FIG. 4 as closest to the esophagus (e.g., lowest) exchange places with electrodes 1 and 2, respectively, as seen in inset 99. In fact, as seen, the half rotation caused all electrodes (apart of 4 and 9) to change heights 96 above the esophagus.

The example GUI shown in FIG. 4 is chosen purely for the sake of conceptual clarity. In alternative embodiments, the GUI may include various highlighting features, such as colors or flashing to alert the physician. In an optional embodiment, the GUI may be drawn over the medical images presented as well to the physician. In an embodiment, the GUI shows, and may update at a given rate, the electrodes arrangement on the display according to their proximity without associating any numerical values to the electrodes arrangement.

Although the embodiments described herein mainly address cardiac ablation procedures, the methods and systems described herein can also be used in other applications, where an a-priori known spatial relationship exist between target tissue and adjacent tissue at risk of thermal damage, such as in neurology procedures.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An apparatus, comprising:
a processor, configured to:
receive one or more medical images that image at least part of an esophagus and at least part of a heart of a patient;
receive positions, within the heart of the patient, of one or more electrodes that apply Radio Frequency (RF) energy to ablate tissue in the heart, in a coordinate system having a vertical axis, the one or more electrodes disposed on an ablation catheter inserted within the heart of the patient;
determine, based on the received positions, a position value for each of the one or more electrodes, the position value based on a location of a position sensor, a location of the one or more electrodes disposed on the ablation catheter, and a position of the esophagus;
determine, based on the determined position values and the received one or more medical images, a height of the one or more electrodes above the esophagus of the patient along the vertical axis;
determine a subset of one or more smallest heights among the calculated heights of the one or more electrodes;
assign a value for each of the calculated heights above the esophagus;
generate a graphical user interface that visualizes the one or more electrodes and their respective heights above the esophagus, the graphical user interface displaying the assigned value for each of the calculated heights;
determine from the subset of one or more smallest heights, at least one electrode positioned within the heart of the patient that is closest to the esophagus; and
adjusting RF energy application to the at least one electrode positioned within the heart of the patient that is closest to the esophagus prior to the application of RF energy to the tissue of the heart.

2. The apparatus according to claim 1, wherein the graphical user interface comprises a diagram that displays a geometrical arrangement of the one or more electrodes.

3. The apparatus according to claim 2, wherein the geometrical arrangement of the one or more electrodes visualizes an actual physical arrangement of the one or more electrodes relative to the esophagus.

4. The apparatus according to claim 1, wherein the graphical user interface displays, for each electrode, a respective identifier.

5. The apparatus according to claim 1, wherein the processor is configured to update the graphical user interface at a given rate or by request.

6. A method, comprising:
in a processor, receiving one or more medical images that image at least part of the esophagus and at least part of the heart;
receiving positions within the heart of a patient, in a coordinate system having a vertical axis, of one or more electrodes that apply Radio Frequency (RF) energy to ablate tissue in the heart, the one or more electrodes disposed on an ablation catheter inserted within the heart of the patient;
determining, based on the received positions, a position value for each of the one or more electrodes, the position value based on a location of a position sensor a location of the one or more electrodes disposed on the ablation catheter, and a position of the esophagus;
determining, based on the determined position values and the received one or more medical images, a height of the one or more electrodes above the esophagus of the patient along the vertical axis;
determining a subset of one or more smallest heights among the calculated heights of the one or more electrodes;
assigning a value for each of the calculated heights of the one or more electrodes;
generating a graphical user interface that visualizes the one or more electrodes and their respective heights above the esophagus, the graphical user interface displaying the assigned value for each of the calculated heights;
displaying the graphical user interface to a user;
determine from the subset of one or more smallest heights at least one electrode positioned within the heart of the patient that is closest to the esophagus; and
adjusting RF energy application to the at least one electrode positioned within the heart of the patient that is closest to the esophagus prior to the application of RF energy to the tissue of the heart.

7. The method according to claim 6, wherein presenting the graphical user interface comprises presenting a diagram displaying a geometrical arrangement of the one or more electrodes.

8. The method according to claim 6, wherein displaying the graphical user interface comprises visualizing an actual physical arrangement of the one or more electrodes relative to the esophagus.

9. The method according to claim 6, wherein displaying the graphical user interface comprises displaying for each electrode a respective identifier.

10. The method according to claim 6, wherein displaying the graphical user interface comprises updating the graphical user interface at a given rate or by request.

\* \* \* \* \*